United States Patent [19]

Sakata et al.

[11] Patent Number: 5,252,576
[45] Date of Patent: Oct. 12, 1993

[54] 1-AMINO-5-HALOGENOURACILS, PROCESS FOR THEIR PREPARATION, AND CENTRAL NERVOUS SYSTEM DEPRESSANTS CONTAINING SAME AS ACTIVE INGREDIENT

[75] Inventors: Shinji Sakata; Masahiro Imaizumi, both of Choshi, Japan

[73] Assignee: Yamasa Shoyu Kabushiki Kaisha, Japan

[21] Appl. No.: 640,413

[22] PCT Filed: Jul. 14, 1989

[86] PCT No.: PCT/JP89/00708
§ 371 Date: Jan. 17, 1991
§ 102(e) Date: Jan. 17, 1991

[87] PCT Pub. No.: WO90/01027
PCT Pub. Date: Feb. 8, 1990

[30] Foreign Application Priority Data

Jul. 18, 1988 [JP] Japan .................. 63-178345
Jul. 18, 1988 [JP] Japan .................. 63-178346
Jul. 18, 1988 [JP] Japan .................. 63-178347

[51] Int. Cl.$^5$ .................. A61K 31/505; C07D 239/02
[52] U.S. Cl. .................. 514/269; 544/313; 544/311
[58] Field of Search .................. 544/313, 311; 514/269

[56] References Cited

U.S. PATENT DOCUMENTS 4,395,406 7/1983 Gacek et al. .................. 544/311
4,396,623 8/1983 Shealy et al. .................. 544/311
4,415,573 11/1983 Ochi et al. .................. 544/311

FOREIGN PATENT DOCUMENTS 93281 4/1987 Japan .

OTHER PUBLICATIONS

Yamamoto et al, Chem Pham. Bull. 33 (9) 4088–4090 (1985).
Shimizu et al, Chem. Pharm. Bull, 35 (12) 4981–4984 (1987).
Tateoka et al, Chem. Pharm Bull 35 (12) 4928–4934 (1987).
Inoué et al, Proc. Natl. Acad. Sci. USA vol. 81, 6240–6244 (1984).

Masahiro Imaizumi et al, Chem. Pharm. Bull 40 (7) 1808–1813 (1992).
Nakamizo et al., Chem. Abst. 107-134623s (1987).

Primary Examiner—Cecilia Tsang
Attorney, Agent, or Firm—Wenderoth, Lind & Ponack

[57] ABSTRACT

Disclosed are a central nervous system depressant which comprises a 1-amino-5-halogenouracil represented by the formula

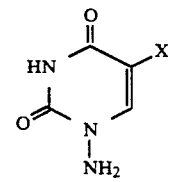

wherein X represents a halogen atom, or a pharmaceutically acceptable salt thereof as an active ingredient; a 1-amino-5-halogenouracil represented by the formula

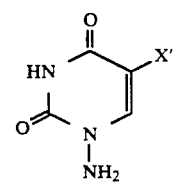

wherein X' represents chlorine, bromine or iodine, or a salt thereof; and
a process for preparing a 1-amino-5-halogenouracil represented by the above shown formula [I] from a pyrimidine derivative represented by the formula

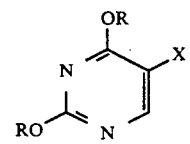

wherein X represents a halogen atom and R represents a protective group.

14 Claims, No Drawings

1-AMINO-5-HALOGENOURACILS, PROCESS FOR THEIR PREPARATION, AND CENTRAL NERVOUS SYSTEM DEPRESSANTS CONTAINING SAME AS ACTIVE INGREDIENT

TECHNICAL FIELD

The present invention relates to a central nervous system depressant containing a 1-amino-5-halogenouracil as an active ingredient, a novel 1-amino-5-halogenouracil useful as a central nervous system depressant, and a novel process for preparing the 1-amino-5-halogenouracil.

BACKGROUND ART

Stress on human body tends to increase with the complication of social environment, and thus an increased number of patients complain of symptoms such as sleep duration disorder, insomnia and the like, which are considered to be induced by stress.

Although the physiological phenomenon named sleep is very complicated and its mechanism has not been elucidated in detail, several nucleic acid-related compounds which affect sleep have been reported. Such compounds include the following:

(1) Uridine

Sleep-promoting effect [see Biomed. Res., 4, 223 (1983); Neurosci. Res., 1, 243 (1984); Proc. Natl. Acad. Sci. U.S.A., 81, 6240 (1984); Neuroscience Letters, 49, 207 (1984)];

(2) Uracil

Hexobarbital induced sleep potentiating effect [see J. Am. Pharm. Assoc., 44, 56 (1955); ibid., 44, 550 (1955)];

(3) $N^3$-Benzyluridine and its derivatives

Hypnotic effect and/or pentobarbital induced sleep potentiating effect [see Chem. Pharm. Bull., 33, 4088 (1985); Japanese Patent Laid-Open Publication No. 207218/1987];

(4) N-Allyl or N-benzyl substituted derivatives of uracil, thymine or 6-methyluracil Hypnotic effect and/or pentobarbital induced sleep potentiating effect [see Chem. Pharm. Bull., 35, 4982 (1987); Abstract of the Proceedings of the 108th Annual Meeting of Pharmaceutical Society of Japan, page 708 (1988)].

It has been also reported that the N-allyl substituted derivative of uracil ($N^1,N^3$-diallyl uracil) and uridine have anticonvulsive effect [see Brain Res., 55, 291 (1973); Chem. Pharm. Bull., 35, 4928 (1987)].

However, these conventional compounds (i) have no hypnotic effect though they exhibit sleep-promoting effect (uridine and uracil), and (ii) must be administered in large doses (320–752 mg/kg) to induce sleep by intraperitoneal injection, and thus they do not always have satisfactory effects.

An object of the present invention is to provide a central nervous system depressant which comprises as an active ingredient a compound exhibiting more potent central nervous system depressant effects such as hypnotic effect, sleep-promoting effect, anticonvulsive effect and the like than the conventional compounds.

DISCLOSURE OF THE INVENTION

We have conducted extensive research in order to discover a compound which has central nervous system sedative effects. As a result, we have found that 1-amino-5-halogenouracil has excellent central nervous system sedative effects.

While 1-amino-5-fluorouracil has hitherto been known as only one 1-amino-5-halogenouracil, it has not been reported that the compound has central nervous system sedative effects [see Sci. Pharm., 52, 46 (1984)].

An object of the present invention is to provide a central nervous system depressant which comprises a 1-amino-5-halogenouracil represented by the formula:

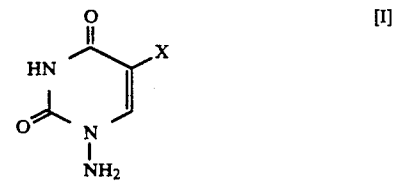

wherein X represents a halogen atom, or a pharmaceutically acceptable salt thereof as an active ingredient.

Another object of the present invention is to provide a novel 1-amino-5-halogenouracil represented by the formula:

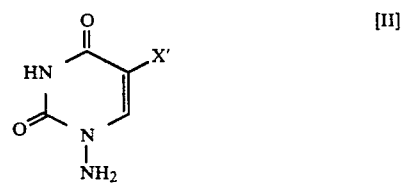

wherein X' represents chlorine, bromine or iodine, or a salt thereof.

A further object of the present invention is to provide a process for preparing a 1-amino-5-halogenouracil represented by the formula [I] shown above which comprises reacting a pyrimidine derivative represented by the formula:

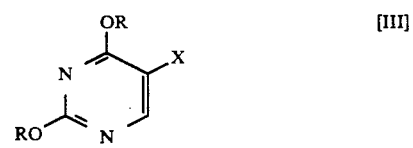

wherein X has the same meaning as defined above and R represents a protective group, with an aminating agent to aminate the 1-position of the pyrimidine derivative, and removing the protective groups.

BEST MODE FOR CARRYING OUT THE INVENTION

The present invention will now be explained in detail below.

The 1-amino-5-halogenouracil which is an active ingredient of the central nervous system depressant of the present invention is the compound represented by the above shown formula [I] (referred to hereinafter simply as "active ingredient of the present pharmaceutical composition").

In the formula [I], the halogen atoms represented by X include fluorine, iodine, bromine and chlorine In this connection, the compounds represented by the formula [I] except for one in which X represents fluorine are novel compounds.

The active ingredient of the present pharmaceutical composition may be in the form of salts and includes acid addition salts with inorganic acids such as hydrochloric acid, hydrobromic acid, sulfuric acid or phosphoric acid, or with organic acids such as citric acid, acetic acid, succinic acid, maleic acid, methanesulfonic acid or p-toluenesulfonic acid.

The active ingredient of the present pharmaceutical composition can be prepared, for example, by the method in which a pyrimidine derivative represented by the following formula [III] is used as a starting compound, which is reacted with an aminating agent (Z-NH$_2$) to give an intermediate [IV] by the specific amination of the 1-position of the pyrimidine derivative (referred to hereinafter as "amination reaction"), and the protective groups represented by R are removed (referred to hereinafter as "deprotection reaction"):

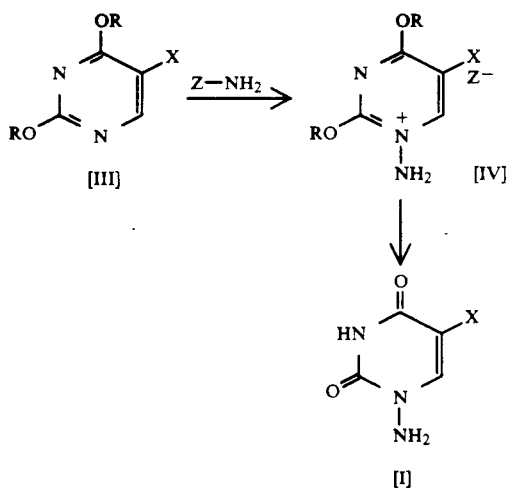

wherein X has the same meanings as defined above, R represents a protective group and Z-NH$_2$ represents an aminating agent.

The halogen atom represented by X in the starting compound may be selected appropriately so that it corresponds to X in the desired compound represented by the formula [I]. The protective groups represented by R include silyl groups such as trimethylsilyl, triethylsilyl, t-butyldimethylsily, methyldiisopropylsilyl and triisopropylsilyl, and alkyl groups such as methyl and ethyl. Particularly, the silyl groups are advantageously used.

The starting compound can be prepared by introducing the protective groups represented by R into a 5-halogenouracil according to a conventional method. For example, when a silyl groupis used as the protective group, protection can be accomplished by using 2- to 10-fold moles of the silylating agent in proportion to 1 mole of the 5-halogenouracil and reacting the mixture in a reaction solvent such as pyridine, picoline, diethylaniline, dimethylaminopyridine, dimethylformamide, acetonitrile, tributylamine, triethylamine or the like, which may be used alone or in admixture thereof, at a reaction temperature in the range of 0° to 50° C. for 1 to 30 hours.

After introducing the protective groups, the pyrimidine derivative represented by the above formula [III] is isolated and purified, if necessary, by a conventional isolation and purification means for nucleic acid bases such as distillation, adsorption chromatography with silica gel or the like, or recrystallization, and then subjected to amination reaction as the starting compound.

The aminating agent (Z-NH$_2$) used for the amination reaction includes hydroxylamines. Specifically, there can be mentioned o-arylsulfonylhydroxylamines such as o-mesitylenesulfonylhydroxylamine, o-(2,4,6-triisopropylbenzenesulfonyl)hydroxylamine, and o-(2-nitrobenzenesulfonyl)hydroxylamine, o-nitrophenylhydroxylamines such as o-(2,4-dinitrophenyl)hydroxylamine and o-picrylhydroxylamine, o-mesitoylhydroxylamine and the like.

The amination reaction with these aminating agents can be accomplished by using 1- to 5-fold moles of an aminating agent, preferably 1- to 1.5-fold moles in proportion to 1 mole of the starting compound and reacting the mixture in a reaction solvent (a halogenated hydrocarbon such as dichloromethane, dichloroethane, or chloroform, an ether type solvent such as tetrahydrofuran, or dioxane, or an aromatic hydrocarbon such as benzene, toluene, or xylene, which may be used alone or in admixture thereof) at a reaction temperature in the range of 0° to 50° C., preferably 0° to 30° C. for 1 to 10 hours.

After the amination reaction, the intermediate [IV] is subjected to deprotection reaction to obtain the active ingredient of the present pharmaceutical composition.

The deprotection reaction may be conducted according to any conventional method for the deprotection of the protective group used. For example, when a silyl group is used as the protective group, it can be removed by ammonium fluoride treatment or acidic or alkaline hydrolysis. Also, when an alkyl group such as methyl or ethyl is used, the alkyl group can be removed by acidic or alkaline hydrolysis.

The active ingredient of the present pharmaceutical composition thus obtained can be isolated and purified by an appropriate combination of conventional isolation and purification means, for example, chromatography such as adsorption chromatography or recrystallization which are applied to the isolation and purification of nucleic acid bases.

While the dose of the compound represented by the formula [I] as the active ingredient of the present pharmaceutical composition depends on many factors such as the severity the patients or acceptability to the composition and finally should be determined by the judgement of doctors, it is generally in the range of 0.05 to 2 g per day for an adult patient, which is administered once or in portions. The route for administration of the composition may be any of appropriate routes such as oral or parenteral administration.

For oral administration, the composition may be in the form of a solid preparation such as powder, granules, capsules or tablets or a liquid preparation such as syrup or elixir. For parenteral administration, the composition may be in the form of injection, suppository, agent for external application or for inhalation. These preparations are prepared according to a conventional method with the addition of a pharmaceutically acceptable preparatory aid to the active ingredient of the present pharmaceutical composition. It is also possible to formulate the composition into a sustained release preparation by a well-known technique.

In the production of the solid preparation for oral administration, the active ingredient of the present pharmaceutical composition is mixed with an excipient such as lactose, starch, crystalline cellulose, calcium lactate, calcium monohydrogenphosphate, magnesium aluminometasilicate or anhydrous silicic acid to give a powder, or, if necessary, the powder is further mixed with a binding agent such as white sugar, hydroxypropylcellulose or polyvinylpyrrolidone, or a disintegrating agent such as carboxymethylcellulose or carboxymethylcellulose calcium for wet or dry granulation to give granules. In the production of tablets, these powders or granules, if necessary, mixed with a lubricant such as magnesium stearate or talc may be punched into tablets. Alternatively, these granules or tablets can be coated with an enteric base such as hydroxypropylmethylcellulose phthalate or a methyl methacrylate copolymer to give enteric-coated preparations, or they can be coated with ethylcellulose, carnauba wax or a hydrogenated oil to give sustained release preparations. Further, in order to prepare capsules, powder or granules may be charged into hard capsules, or the active ingredient of the present pharmaceutical composition is first dissolved in glycerol, polyethylene glycol, sesame oil, olive oil or the like and next coated with a gelatin film to give soft capsules.

In order to prepare the liquid preparation for oral administration, the active ingredient of the present pharmaceutical preparation and a sweetener such as white sugar, sorbitol or glycerol may be dissolved in water to give a clear syrup, or the syrup may be further mixed with an essential oil or ethanol to give an elixir or with gum arabic, tragacanth gum, polysorbate 80, or carboxymethylcellulose sodium to give an emulsion or a suspension. These liquid preparations may also contain flavoring agents, colorants, preservatives or the like, if desired.

In order to prepare the preparation for injection, the active ingredient of the present pharmaceutical composition may be dissolved in distilled water for injection, if necessary, together with a pH adjusting agent such as sodium hydroxide, hydrochloric acid, lactic acid, sodium lactate, sodium monohydrogenphosphate or sodium dihydrogenphosphate, and an isotonizing agent such as sodium chloride or glucose, aseptically filtered and charged into ampoules, or these solutions may be mixed with mannitol, dextrin, cyclodextrin, or gelatin and lyophilized under vacuum to give injections which should be dissolved on use. Furthermore, the active ingredient of the present pharmaceutical composition can be mixed with lecithin, polysorbate 80, or polyoxyethylenehydrogenated castor oil, and the mixture is emulsified in water to give an emulsion for injection.

In order to prepare the preparation for rectal administration, the active ingredient of the present pharmaceutical composition may be melted by heating together with a suppository base such as tri-, di- or mono-glycerides of cacao fatty acid or polyethylene glycol, poured into a mold and cooled, or the active ingredient of the present pharmaceutical composition may be dissolved into polyethylene glycol or soybean oil and coated with a gelatin film.

In order to prepare the preparation for external application, the active ingredient of the present pharmaceutical composition is added to white vaseline, beeswax, liquid paraffin or polyethylene glycol and the mixture is kneaded, if necessary, under heat to give an ointment, or it is kneaded with an adhesive such as rosin or an alkyl acrylate polymer and then spread over nonwoven fabrics made of, for example, polyethylene to give a tape preparation.

The present invention will be illustrated below with reference to Synthesis Examples, Test Examples and Preparation Examples.

SYNTHESIS EXAMPLE 1

1-Amino-5-fluorouracil

5-Fluorouracil was silylated as usual with hexamethyldisilazane, and then 8.8 g (32 mmole) of 2,4-ditrimethylsilyloxy-5-fluoropyrimidine thus obtained, distilled and purified was dissolved in dichloromethane (48 ml). To the solution was added 7.5 g (35 mmole) of mesitylenesulfonylhydroxylamine (MSH) under ice-cooling, and the mixture was reacted with stirring at room temperature for 4 hours.

After reaction, the reaction solution was concentrated under reduced pressure. Distilled water (200 ml) was added to the residue, and oily impurities were extracted with chloroform (50 ml) from the mixture. The aqueous phase was neutralized with a weakly basic resin and then concentrated to dryness under reduced pressure.

The crude crystal thus obtained was purified by sublimation under the conditions of 150° C. and 5 mmHg to give 2.9 g (yield, 62%) of 1-amino-5-fluorouracil.

The product was further recrystallized from 50% ethanol to give colorless needle crystals.

M.P. 196–199° C. (lit. 205–207° C.)
Elementary analysis for $C_4H_4N_3O_2F$:
Calculated (%): C, 33.11; H, 2.78; N, 28.96;
Found (%): C, 33.15; H, 2.79; N, 28.78;

SYNTHESIS EXAMPLE 2

1-Amino-5-bromouracil

After the silylation of 5-bromouracil conducted in the same manner as in Synthesis Example 1, 8.8 g (26 mmole) of 5-bromo-2,4-ditrimethylsilyloxypyrimidine distilled and purified was dissolved in 50 ml of dichloromethane. To the solution was added 6.7 g (31 mmole) of MSH under ice-cooling, and the mixture was reacted with stirring at room temperature for 4 hours.

After reaction, the reaction solution was concentrated under reduced pressure. To the residue were added distilled water (200 ml) and subsequently 2N-sodium hydroxide to adjust the pH to 6.0, and the solution was concentrated under reduced pressure.

The crude product thus obtained was collected by filtration and recrystallized from 50% ethanol to give 3 g (yield, 55%) of crystalline 1-amino-5-bromouracil.

M.P.: 214–215° C.
Elementary analysis for $C_4H_4N_3O_2Br$;
Calculated (%): C, 23.32; H, 1.96; N, 20.40;
Found (%): C, 23.59; H, 1.97; N, 20.14;
NMR spectrum ($\delta$, ppm, DMSO-$d_6$):
5.54 (2H, s, $NH_2$, disappeared by the addition of $D_2O$)
8.14 (1H, s, 6-H)
11.84 (1H, s, NH, disappeared by the addition of $D_2O$)

SYNTHESIS EXAMPLE 3

1-Amino-5-chlorouracil

Starting from 5-chlorouracil, 1-amino-5-chlorouracil was obtained in the same manner as in Synthesis Example 2.

M.P.: 224–225° C. (recrystallized from water)
Elementary analysis for $C_4H_4N_3O_2Cl$;
Calculated (%): C, 29.74; H, 2.50; N, 26.01;
Found (%): C, 29.83; H, 2.55; N, 25.93;

NMR spectrum (δ, ppm, DMSO-d$_6$):
5.54 (2H, s, NH$_2$, disappeared by the addition of D$_2$O)
8.09 (1H, s, 6-H)
11.86 (1H, s, disappeared by the addition of D$_2$O)

SYNTHESIS EXAMPLE 4

1-Amino-5-iodouracil

Starting from 5-iodouracil, 1-amino-5-iodouracil was obtained in the same manner as in Synthesis Example 2.
M.P.: 195–196° C. (recrystallized from water)
Elementary analysis for C$_4$H$_4$N$_3$O$_2$I:
Calculated (%): C, 18.99; H, 1.59; N, 16.61;
Found (%): C, 19.05; H, 1.57; N, 16.51;
NMR spectrum (δ, ppm, DMSO-d$_6$):
5.51 (2H, s, NH$_2$, disappeared by the addition of D$_2$O)
8.08 (1H, s, 6-H)
11.69 (1H, s, disappeared by the addition of D$_2$O)

TEST EXAMPLE 1

Hypnotic effect

The following compounds suspended in a physiological saline solution containing 0.5% carboxymethylcellulose were administered to ICR mice (male).

The time from the loss of righting reflex until the recovery of its (sleeping time) was measured. The results are shown in Table 1.

TABLE 1

| Compound | Dose (mg/kg) | Route of Administration* | No. of Animals | Mean Sleeping Time (min) |
|---|---|---|---|---|
| 1-Amino-5-fluorouracil | 100 | ip | 2 | 53 |
| 1-Amino-5-fluorouracil | 100 | po | 3 | 21 |
| 1-Amino-5-bromouracil | 112 | ip | 2 | 80 |
| 1-Amino-5-chlorouracil | 200 | po | 1 | 14 |

*ip = intraperitoneal; po = peroral

TEST EXAMPLE 2

Anticonvulsive effect a) Thiosemicarbazide induced convulsion

Thiosemicarbazide (20 mg/kg) was administered intraperitoneally to ICR mice (male), and 30 minutes thereafter the following compounds suspended in a physiological saline solution containing 0.5% carboxymethylcellulose were administered subcutaneously. The time required for initiating convulsion (initial convulsion time) was measured. Physiological saline containing no test compounds was used as a control. The results are shown in Table 2.

TABLE 2

| Compound | Dose (mg/kg) | No. of Animals | Initial Convulsion Time (min) |
|---|---|---|---|
| 1-Amino-5-fluorouracil | 50 | 4 | 80.9 ± 12.9* |
| 1-Amino-5-bromouracil | 50 | 8 | 118.3 ± 6.9** |
| Control | — | 4 | 60.3 ± 6.8 |

*: significant at a significant level of 5% or less
**: significant at a significant level of 0.5% or less b) Picrotoxin induced convulsion The following compounds suspended in a physiological saline solution containing 0.5% carboxymethylcellulose were administered intraperitoneally to ICR mice (male). Immediately thereafter, picrotoxin was also administered intraperitoneally in the same manner, and the number of convulsions per hour and lethality of the animals within 1 hour after the administration of picrotoxin were examined. Physiological saline containing no test compounds were used as a control. The results are shown in Table 3.

TABLE 3

| Compound | Dose (mg/kg) | No. of Animals | No. of Convulsions | Lethality (%) |
|---|---|---|---|---|
| 1-Amino-5-bromouracil | 10 | 5 | 1.3 ± 1.0* | 20 |
| 1-Amino-5-bromouracil | 20 | 8 | 1.8 ± 1.7* | 0** |
| Control | — | 8 | 5.6 ± 0.9 | 75 |

*: significant at a significant level of 0.1% or less
**: significant at a significant level of 1% or less

TEST EXAMPLE 3

Acute toxicity

1-Amino-5-bromouracil was suspended in a physiological saline solution containing 0.5% carboxymethylcellulose. 500 mg/kg of the compound was administered intraperitoneally to 8 ICR mice, and lethality of the animals was observed for 1 week. As a result, all of the mice survived with no lethality.

PREPARATION EXAMPLE 1

Tablet

| | |
|---|---|
| 1-Amino-5-bromouracil | 10 g |
| Corn starch | 65 g |
| Carboxymethylcellulose | 20 g |
| Polyvinylpyrrolidone | 3 g |
| Calcium stearate | 2 g |
| Total | 100 g |

Tablets each weighing 100 mg are prepared in a conventional manner. Each tablet contains 10 mg of 1-amino-5-bromouracil.

PREPARATION EXAMPLE 2

Powder and Capsule

| | |
|---|---|
| 1-Amino-5-fluorouracil | 20 g |
| Crystalline cellulose | 80 g |
| Total | 100 g |

Both the powders are mixed into a powder preparation. Separately, 100 mg of the preparation is charged into a No. 5 hard capsule to form a capsule preparation.

INDUSTRIAL APPLICABILITY

The active ingredient of the present pharmaceutical composition, as apparent from the aforementioned Test Examples, has the following characteristics as compared with conventional compounds and is very useful as a central nervous system depressant.

(i) A little dose of the active ingredient of the present pharmaceutical composition induces central nervous system depressant effects such as hypnotic effect or anticonvulsive effect.

In order to induce hypnotic effect by intraperitoneal administration, a dose of 320 to 752 mg is required for conventional compounds. For example, the doses of 433 mg, 320 mg and 752 mg per kg body weight were required for N$^1$,N$^3$-diallyluracil, N$^1$-methoxymethyl-N$^3$- benzyluracil and N³-benzyl-2',3',5'-tri-o-methyluridine, respectively.

On the other hand, 1-amino-5-halogenouracil, the active ingredient of the present pharmaceutical composition, can induce sleep with a dose of about 100 mg per kg body weight.

(ii) The active ingredient of the present pharmaceutical composition can express its activity by oral administration. Hitherto, there have been reported no nucleic acid-related substances having hypnotic effect by oral administration.

(iii) The active ingredient of the present pharmaceutical composition is a compound which has an extremely low toxicity. The simultaneous production of both the 1-amino derivative and the 1,3-diamino derivative which is a defect in the conventional method [Sci. Pharm., 52. 46 (1984)] is suppressed by the synthesis method of the present invention, and the 1-position of pyrimidines can be specifically aminated to give 1-amino-5-halogenouracil in a high yield.

What is claimed is:

1. A central nervous system depressant which comprises an effective amount of a 1-amino-5-halogenouracil represented by the formula

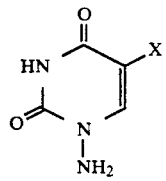

[I]

wherein X represents a halogen atom selected from the group consisting of chlorine, bromine and iodine, or a pharmaceutically acceptable salt thereof as an active ingredient and a pharmaceutically acceptable carrier.

2. A 1-amino-5-halogenouracil represented by the formula

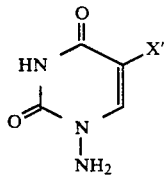

[II]

wherein X' represents chlorine, bromine or iodine, or a pharmaceutically acceptable salt thereof.

3. A process for preparing a 1-amino-5-halogenouracil represented by the formula

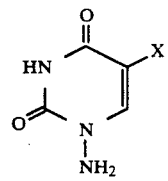

[I]

wherein X represents a halogen atom, which comprises reacting a pyrimidine derivative represented by the formula

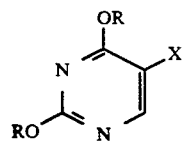

[III]

wherein X represents a halogen atom and R represents a protective group selected from the group consisting of a silyl group and an alkyl group,
with a hydroxylamine to aminate the 1-position of the pyrimidine derivative, and removing the protective groups.

4. A method of treating a patient requiring central nervous system depression which comprises administering to said patient, a therapeutically effective amount of a central nervous system depressant comprising as an active ingredient an effective amount of a 1-amino-5-halogenouracil represented by the formula

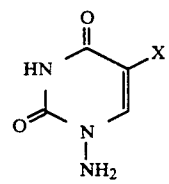

[I]

wherein X represents a halogen atom, or a pharmaceutically acceptable salt thereof.

5. The central nervous system depressant as claimed in claim 1, wherein X represents bromine.

6. The 1-amino-5-halogenouracil or a pharmaceutically acceptable salt thereof as claimed in claim 2, wherein X represents bromine.

7. The central nervous system depressant as claimed in claim 1, wherein X represents chlorine.

8. The central nervous system depressant as claimed in claim 1, wherein X represents iodine.

9. The 1-amino-5-halogenouracil or a pharmaceutically acceptable salt thereof as claimed in claim 2, wherein X represents chlorine.

10. The 1-amino-5-halogenouracil or a pharmaceutically acceptable salt thereof as claimed in claim 2, wherein X represents iodine.

11. A method of treating a patient requiring central nervous system depression as claimed in claim 4, wherein X represents fluorine.

12. A method of treating a patient requiring central nervous system depression as claimed in claim 4, wherein X represents chlorine.

13. A method of treating a patient requiring central nervous system depression as claimed in claim 4, wherein X represents bromine.

14. A method of treating a patient requiring central nervous system depression as claimed in claim 4, wherein X represents iodine.

* * * * *